US006451807B1

(12) United States Patent
Emmick et al.

(10) Patent No.: US 6,451,807 B1
(45) Date of Patent: Sep. 17, 2002

(54) METHODS OF TREATING SEXUAL DYSFUNCTION IN AN INDIVIDUAL SUFFERING FROM A RETINAL DISEASE, CLASS 1 CONGESTIVE HEART FAILURE, OR MYOCARDIAL INFARCTION USING A PDE5 INHIBITOR

(75) Inventors: Jeffrey T. Emmick, Plainfield, IN (US); Kenneth M. Ferguson, Bothell, WA (US); William E. Pullman, Carmel, IN (US); John S. Whitaker, Woodinvill, WA (US)

(73) Assignee: Lilly Icos, LLC., Wilmington, DE (US)

( * ) Notice: Subject to any disclaimer, the term of this patent is extended or adjusted under 35 U.S.C. 154(b) by 0 days.

(21) Appl. No.: 09/558,911

(22) Filed: Apr. 26, 2000

Related U.S. Application Data

(60) Provisional application No. 60/132,036, filed on Apr. 30, 1999.

(51) Int. Cl.$^7$ ............................................. A61K 31/44
(52) U.S. Cl. ....................................................... 514/287
(58) Field of Search ........................................ 514/287

(56) References Cited

U.S. PATENT DOCUMENTS

| | | | |
|---|---|---|---|
| 4,931,445 A | 6/1990 | Goldstein et al. | 514/252 |
| 5,702,936 A | 12/1997 | Beavo et al. | 435/196 |
| 5,859,006 A | 1/1999 | Daugan | 514/249 |
| 5,981,527 A | 11/1999 | Daugan et al. | 514/250 |
| 5,985,326 A | 11/1999 | Butler | 424/484 |
| 6,001,847 A | 12/1999 | Daugan et al. | 514/287 |

FOREIGN PATENT DOCUMENTS

| | | | | |
|---|---|---|---|---|
| CA | 2020630 | 1/1991 | | C07D/487/04 |
| WO | WO-96/32003 | * 10/1996 | | |
| WO | WO 97/03675 | * 2/1997 | | |
| WO | WO 97/43287 | 11/1997 | | C07D/471/04 |
| WO | WO 00/15639 | 3/2000 | | C07D/471/04 |

OTHER PUBLICATIONS

Viagra, US Product Prescribing Information 2000.*
Gennaro et al, Ed., Remington: The Science and Practice of Pharmacy, 19th Ed., 1995, p. 806.*
I. Goldstein et al., *The New England Journal of Medicine*, vol. 338, No. 20, pp. 1397–1404 (1998).
S.A. Ballard et al., *The Journal of Urology*, vol. 159, pp. 2164–2171 (1998).
Product insert, Viagra® Tablets (2000).
*Physicians' Desk Reference*, 53 Edition, 1999, pp. 2424–2427.
Rosen et al., The international index of erectile function (IIEF): A multidimensional scale for assessment of erectile dysfunction, *Urology*, 49(6), pp. 822–830 (1997).
K.J. Murray, Phosphodiesterase PDE $V_A$ inhibitors, *DN&P*, 6(3), pp. 150–156 (1993).
A. Taher et al. *J. Urology*, 149:285a, AUA Eighty–Eighth Annual Meeting, May, 1993.
M. Boolell et al., Sildenafil: an orally active type 5 cyclic GMP–specific phosphodiesterase inhibitor for the treatment of penile erectile dysfunction, *Int. J. of Impotence Res.*, 8, pp. 47–52 (1996).
A.M. Martel et al., Treatment of erectile dysfunction phosphodiesterase V inhibitor, *Drugs of the Future*, 22(2), pp. 138–143 (1997).
J.N. Wells et al., Cyclic nucleotide, phophodiesterase activities of pig coronary arteries, *Biochim. Biophys. Acta*, 384, pp. 430–442 (1975).
A. Sitaramayya et al., On the mechanism of light activation of retinal rod outer segments cyclic GMP phosphodiesterase (light activation–influence of bleached rhodopsin and KF–deinhibition), *Exp. Eye Res.*, 25, pp. 163–169 (1977).
N. Virmaux et al., Proteins of bovine retinal outer segments: electrophoresis on polyacrylamide gels in the presence of sodium dodecyl sulfate, *FEBS Letters*, 12(6), pp. 325–328 (1971).
K. Loughney et al., Isolation and characterization of cDNAs corresponding to two human calcium, calmodulin–regulated, 3',5'–cyclic nucleotide phosphodiesterases, *The Journal of Biological Chemistry*, 271(2), pp. 796–806 (1996).
Y.C. Cheng et al., Relationship between the inhibition constant ($K_i$) and the concentration of inhibitor which causes 50 per cent [six] inhibition ($I_{50}$) of an enzymatic reaction, *Biochem. Pharmacol.*, 22, pp. 3099–3108 (1973).
D. Webb et al., Sildenafil citrate and blood–pressure–lowering drugs: regults of drug interaction studies with an organic nitrate and a calcium antagonist, *Amer. J. of Cardiology*, 83 (5A), pp. 21C–28C (1999).
V. Price et al., Expression of heterologous proteins in *Saccharomyces cerevisiae* using the ADH2 promoter, *Methods in Enzymology*, 185, pp. 308–318 (1990).
H. Shichi et al., Biochemistry of visual pigments, *J. Biol. Chem.*, 244(3), pp. 529–536 (1969).
C. Conti et al., *Amer. J. of Cardiology*, 83(5A), 29C–34C (Mar. 4, 1999).

* cited by examiner

*Primary Examiner*—Russell Travers
*Assistant Examiner*—Mojdeh Bahar
(74) *Attorney, Agent, or Firm*—Marshall, Gerstein & Borun.

(57) ABSTRACT

The present invention relates to highly selective phosphodiesterase (PDE) enzyme inhibitors and to their use in methods of treating sexual dysfunction in individuals suffering from a retinal disease, class 1 congestive heart failure, or myocardial infarction.

7 Claims, No Drawings

METHODS OF TREATING SEXUAL DYSFUNCTION IN AN INDIVIDUAL SUFFERING FROM A RETINAL DISEASE, CLASS 1 CONGESTIVE HEART FAILURE, OR MYOCARDIAL INFARCTION USING A PDE5 INHIBITOR

CROSS REFERENCE TO RELATED APPLICATIONS

This application claims the benefit of provisional patent application Ser. No. 60/132,036, filed Apr. 30, 1999.

FIELD OF THE INVENTION

The present invention relates to highly selective phosphodiesterase (PDE) enzyme inhibitors and to their use in pharmaceutical articles of manufacture. In particular, the present invention relates to potent inhibitors of cyclic guanosine 3',5'-monophosphate specific phosphodiesterase type 5 (PDE5) that when incorporated into a pharmaceutical product are useful for the treatment of sexual dysfunction. The articles of manufacture described herein are characterized by selective PDE5 inhibition, and accordingly, provide a benefit in therapeutic areas where inhibition of PDE5 is desired, with minimization or elimination of adverse side effects resulting from inhibition of other phosphodiesterase enzymes.

BACKGROUND OF THE INVENTION

The biochemical, physiological, and clinical effects of cyclic guanosine 3',5'-monophosphate specific phosphodiesterase (cGMP-specific PDE) inhibitors suggest their utility in a variety of disease states in which modulation of smooth muscle, renal, hemostatic, inflammatory, and/or endocrine function is desired. Type 5 cGMP-specific phosphodiesterase (PDE5) is the major cGMP hydrolyzing enzyme in vascular smooth muscle, and its expression in penile corpus cavernosum has been reported (Taher et al., *J. Urol.*, 149:285A (1993)). Thus, PDE5 is an attractive target in the treatment of sexual dysfunction (Murray, *DN&P* 6(3): 150–56 (1993)).

A pharmaceutical product, which provides a PDE5 inhibitor, is currently available and marketed under the trademark VIAGRA®. The active ingredient in VIAGRA® is sildenafil. The product is sold as an article of manufacture including 25, 50, and 100 mg tablets of sildenafil and a package insert. The package insert provides that sildenafil is a more potent inhibitor of PDE5 than other known phosphodiesterases (greater than 80 fold for PDE1 inhibition, greater than 1,000 fold for PDE2, PDE3, and PDE4 inhibition). The $IC_{50}$ for sildenafil against PDE5 has been reported as 3 nM (*Drugs of the Future*, 22(2), pp. 128–143 (1997)), and as 3.9 nM (Boolell et al., *Int. J. of Impotence Res.*, 8 p. 47–52 (1996)). N.C. Sildenafil is described as having a 4,000-fold selectivity for PDE5 versus PDE3, and only a 10-fold selectivity for PDE5 versus PDE6. Its relative lack of selectivity for PDE6 is theorized to be the basis for abnormalities related to color vision.

While sildenafil has obtained significant commercial success, it has fallen short due to its significant adverse side effects, including facial flushing (10% incidence rate). Adverse side effects limit the use of sildenafil in patients suffering from visual abnormalities, hypertension, and, most significantly, by individuals who use organic nitrates (Welds et al., *Amer. J. of Cardiology*, 83 (5A), pp. 21(C)–28(C) (1999)).

The use of sildenafil in patients taking organic nitrates is believed to cause a clinically significant drop in blood pressure which could place the patient in danger. Accordingly, the package label for sildenafil provides strict contraindications against its use in combination with organic nitrates (e.g., nitroglycerin, isosorbide mononitrate, isosorbide dinitrate, erythrityl tetranitrate) and other nitric oxide donors in any form, either regularly or intermittently, because sildenafil potentiates the hypotensive effects of nitrates. See C. R. Conti et al., *Amer. J. of Cardiology*, 83(5A), pp. 29C–34C (1999). Thus, even with the availability of sildenafil, there remains a need to identify improved pharmaceutical products that are useful in treating sexual dysfunction.

The present invention provides an article of manufacture for human pharmaceutical use, comprising a package insert, a container, and an oral dosage form comprising a selective PDE5 inhibitor at unit dosages between about 1 and about 20 mg/dosage form. The beneficial effects of the present invention were observed in clinical studies and through the discovery that a selective PDE5 inhibitor meeting the following criteria allows for the effective oral administration of about 1 to about 20 mg/dosage form without contraindications generally required for PDE5 inhibitor products, such as warnings directed to vision abnormalities. A selective PDE5 inhibitor of the present invention exhibits:

1) at least a 100 fold differential in the $IC_{50}$ values for the inhibition of PDE5 versus PDE6 for a particular PDE5 inhibitor (i.e., the $IC_{50}$ value versus PDE5 is at least 100 times less than the $IC_{50}$ value versus PDE6);
2) at least a 1000 fold differential in the $IC_{50}$ values for the inhibition of PDE5 versus PDE1c; and
3) an $IC_{50}$ value less than 10 nM.

Significantly, clinical studies also revealed that an effective product having a reduced tendency to cause flushing in susceptible individuals can be provided. Most unexpectedly, the product also can be administered with clinically insignificant side effects associated with the combined effects of a PDE5 inhibitor and an organic nitrate. Thus, the contraindication once believed necessary for a product containing a PDE5 inhibitor is unnecessary when a selective PDE5 inhibitor, as defined above, is used as disclosed herein. Thus, the present invention provides an effective therapy for sexual dysfunction in individuals who previously were untreatable or suffered from unacceptable side effects, including individuals having cardiovascular disease, such as in individuals requiring nitrate therapy, having suffered a myocardial infarction more than three months before the onset of sexual dysfunction therapy, and suffering from class 1 congestive heart failure as defined by the New York Heart Association (NYHA), or individuals suffering from vision abnormalities.

SUMMARY OF THE INVENTION

The present invention provides an article of manufacture for human pharmaceutical use, comprising a package insert, a container, and an oral dosage form comprising about 1 to about 20 mg of a selective PDE5 inhibitor per dosage form.

The present invention further provides a method of treating conditions where inhibition of PDE5 is desired, which comprises administering to a patient in need thereof an oral dosage form containing about 1 to about 20 mg of a selective PDE5 inhibitor, as needed, up to a total dose of 20 mg/-day. The invention further provides the use of an oral dosage form comprising a selective PDE5 inhibitor at a dosage of about 1 to about 20 mg for the treatment of sexual dysfunction.

Specific conditions that can be treated by the method and article of the present invention, include, but are not limited to, male erectile dysfunction and female sexual dysfunction, particularly female arousal disorder, also known as female sexual arousal disorder.

In particular, the present invention provides an article of manufacture for human pharmaceutical use comprising:
(a) an oral dosage form comprising about 1 to about 20 mg of a selective PDE5 inhibitor having
   (i) at least a 100 fold differential in $IC_{50}$ values for the inhibition of PDE5 versus PDE6,
   (ii) at least a 1000 fold differential in $IC_{50}$ values for the inhibition of PDE5 versus PDE1c,
   (iii) an $IC_{50}$ less than 10 nM, and
   (iv) sufficient bioavailability to be effective in about 1 to about 20 mg unit oral dosages;
(b) a package insert providing that the PDE5 inhibitor is useful to treat sexual dysfunction in a patient in need thereof, and that is free of contradictions associated with administration of organic nitrates; and
(c) a container.

The present invention further provides an article of manufacture for human pharmaceutical use comprising:
(a) an oral dosage form comprising about 1 to about 20 mg of selective PDE5 inhibitor having
   (i) at least a 100 fold differential in $IC_{50}$ values for the inhibition of PDE5 versus PDE6,
   (ii) at least a 1000 fold differential in $IC_{50}$ values for the inhibition of PDE5 versus PDE1c,
   (iii) an $IC_{50}$ less than 10 nM, and
   (iv) a sufficient bioavailability to be effective in about 1 to about 20 mg unit oral dosages;
(b) a package insert providing that the PDE5 inhibitor is useful to treat sexual dysfunction in a patient in need thereof and that is using an organic nitrate; and
(c) a container.

The present invention also provides an article of manufacture for human pharmaceutical use comprising:
(a) an oral dosage form comprising about 1 to about 20 mg of a selective PDE5 inhibitor having
   (i) at least a 100 fold differential in $IC_{50}$ values for the inhibition of PDE5 versus PDE6,
   (ii) at least 1000 fold differential in $IC_{50}$ values for the inhibition of PDE5 versus PDE1c,
   (iii) an $IC_{50}$ less than 10 nM, and
   (iv) a sufficient bioavailability to be effective in about 1 to about 20 mg unit oral dosages;
(b) a package insert providing that the PDE5 inhibitor is useful to treat sexual dysfunction in a patient in need thereof and that is suffering from a condition selected from the group consisting of a retinal disease, proneness to flushing, proneness to vision abnormalities, class 1 congestive heart failure, a myocardial infarction 90 days or more before onset of the sexual dysfunction treatment, and combinations thereof; and
(c) a container.

DETAILED DESCRIPTION

For purposes of the present invention as disclosed and described herein, the following terms and abbreviations are defined as follows.

The term "container" means any receptacle and closure therefor suitable for storing, shipping, dispensing, and/or handling a pharmaceutical product.

The term "$IC_{50}$" is the measure of potency of a compound to inhibit a particular PDE enzyme (e.g., PDE1c, PDE5, or PDE6). The $IC_{50}$ is the concentration of a compound that results in 50% enzyme inhibition in a single dose-response experiment. Determining the $IC_{50}$ value for a compound is readily carried out by a known in vitro methodology generally described in Y. Cheng et al., *Biochem. Pharmacol.,* 22, pp. 3099–3108 (1973).

The term "package insert" means information accompanying the product that provides a description of how to administer the product, along with the safety and efficacy data required to allow the physician, pharmacist, and patient to make an informed decision regarding use of the product. The package insert generally is regarded as the "label" for a pharmaceutical product.

The term "oral dosage form" is used in a general sense to reference pharmaceutical products administered orally. Oral dosage forms are recognized by those skilled in the art to include such forms as liquid formulations, tablets, capsules, and gelcaps.

The term "selective PDE5 inhibitor" is defined as a PDE5 inhibitor having:
1) an $IC_{50}$ value for the inhibition of PDE5 at least 100 times less than the $IC_{50}$ value for the inhibition of PDE6;
2) an $IC_{50}$ value for the inhibition of PDE5 at least 1,000 times less than the $IC_{50}$ value for the inhibition of PDE1c; and
3) an $IC_{50}$ value for the inhibition of PDE5 less than 10 nM. Selective PDE5 inhibitors vary significantly in chemical structure, and their use in the present invention is not dependent on chemical structure, but rather on the selectivity and potency parameters disclosed herein.

The term "vision abnormalities" means abnormal vision characterized by blue-green vision believed to be caused by PDE6 inhibition.

The term "flushing" means an episodic redness of the face and neck attributed to vasodilation caused by the ingestion of a drug, usually accompanied by a feeling of warmth over the face and neck and sometimes accompanied by perspiration.

The term "free drug" means solid particles of drug not intimately embedded in a polymeric co-precipitate.

As previously stated, the present invention is directed to an article of manufacture for human pharmaceutical use, comprising a package insert, a container, and a dosage form comprising about 1 to about 20 mg of a selective PDE5 inhibitor per unit dosage form. A selective PDE5 inhibitor useful in the present invention is a PDE5 inhibitor having:
1) at least a 100 fold differential in $IC_{50}$ values for the inhibition of PDE5 versus PDE6;
2) at least a 1000 fold differential in $IC_{50}$ values for the inhibition of PDE5 versus PDE1c; and
3) an $IC_{50}$ value less than 10 nM; and is sufficiently bioavailable to be effective in about 1 to about 20 mg unit dosages.

The differential is expressed as a PDE6/PDE5 ratio of $IC_{50}$ values, i.e., the ratio of the $IC_{50}$ value versus PDE6 to the $IC_{50}$ value versus PDE5 (PDE6/PDE5) is greater than 100, more preferably greater than 300, and most preferably greater than 500.

Similarly, the ratio of $IC_{50}$ value versus PDE1c to $IC_{50}$ value versus PDE5 (PDE1c/PDE5) is greater than 1000. Preferred PDE5 inhibitors have a greater than 3,000 fold differential between the inhibition of PDE5 and PDE1c, more preferably greater than a 5,000 fold differential between $IC_{50}$ value versus PDE5 and PDE1c. The potency of the inhibitor, as represented by the $IC_{50}$ value versus PDE5, is less than 10 nM, preferably less than 5 nM, more preferably less than 2 nM, and most preferably less than 1 nM.

The package insert provides a description of how to administer a pharmaceutical product, along with the safety and efficacy data required to allow the physician, pharmacist, and patient to make an informed decision regarding the use of the product. The package insert generally is regarded as the label of the pharmaceutical product. The package insert incorporated into the present article of manufacture indicates that the selective PDE5 inhibitor is useful in the treatment of conditions wherein inhibition of PDE5 is desired. The package insert also provides instructions to administer one or more about 1 to about 20 mg unit dosage forms as needed, up to a maximum total dose of 20 mg per day. Preferably, the dose administered is about 5 to about 20 mg/day, more preferably about 5 to about 15 mg, and most preferably an about 5 mg or about 10 mg dosage form administered once per day, as needed.

Preferred conditions to be treated include sexual dysfunction (including male erectile dysfunction; and female sexual dysfunction, and more preferably female arousal disorder (FAD)). The preferred condition to be treated is male erectile dysfunction.

Significantly, the package insert supports use of the product to treat sexual dysfunction in patients suffering from a retinal disease, for example diabetic retinopathy or retinitis pigmentosa, or in patients who are using organic nitrates. Thus, the package insert preferably is free of contraindications associated with these conditions, and particularly the administration of the dosage form with an organic nitrate. More preferably, the package insert also is free of any cautions or warnings both associated with retinal diseases, particularly retinitis pigmentosa, and associated with individuals prone to vision abnormalities. Preferably, the package insert also reports incidences of flushing below 2%, preferably below 1%, and most preferably below 0.5%, of the patients administered the dosage form. The incidence rate of flushing demonstrates marked improvement over prior pharmaceutical products containing a PDE5 inhibitor.

The container used in the present article of manufacture is conventional in the pharmaceutical arts. Generally, the container is a blister pack, foil packet, glass or plastic bottle and accompanying cap or closure, or other such article suitable for use by the patient or pharmacist. Preferably, the container is sized to accommodate 1–1000 solid dosage forms, preferably 1 to 500 solid dosage forms, and most preferably, 5 to 30 solid dosage forms.

Oral dosage forms are recognized by those skilled in the art to include, for example, such forms as liquid formulations, tablets, capsules, and gelcaps. Preferably the dosage forms are solid dosage forms, particularly, tablets comprising about 1 to about 20 mg of a selective PDE5 inhibitor. Any pharmaceutically acceptable excipients for oral use are suitable for preparation of such dosage forms. Suitable pharmaceutical dosage forms include coprecipitate forms described, for example, in Butler U.S. Pat. No. 5,985,326, incorporated herein by reference. In preferred embodiments, the unit dosage form of the present invention is a solid free of a coprecipitate form of the PDE5 inhibitor, but rather contains a solid PDE5 inhibitor as a free drug.

Preferably, the tablets comprise pharmaceutical excipients generally recognized as safe such as lactose, microcrystalline cellulose, starch, calcium carbonate, magnesium stearate, stearic acid, talc, and colloidal silicon dioxide, and are prepared by standard pharmaceutical manufacturing techniques as described in *Remington's Pharmaceutical Sciences*, 18th Ed., Mack Publishing Co., Easton, Pa. (1990). Such techniques include, for example, wet granulation followed by drying, milling, and compression into tablets with or without film coating; dry granulation followed by milling, compression into tablets with or without film coating; dry blending followed by compression into tablets, with or without film coating; molded tablets; wet granulation, dried and filled into gelatin capsules; dry blend filled into gelatin capsules; or suspension and solution filled into gelatin capsules. Generally, the solid dosage forms have identifying marks which are debossed or imprinted on the surface.

The present invention is based on detailed experiments and clinical trials, and the unexpected observations that side effects previously believed to be indicative of PDE5 inhibition can be reduced to clinically insignificant levels by the selection of a selective PDE5 inhibitor having the specific characteristics outlined herein, namely:

1) at least a 100 fold differential in the $IC_{50}$ values for the inhibition of PDE5 versus PDE6;
2) at least a 1000 fold differential in the $IC_{50}$ values for the inhibition of PDE5 versus PDE1c; and
3) an $IC_{50}$ value for the inhibition of PDE5 less than 10 nM.

This unexpected observation enabled the development of articles of manufacture that incorporate a selective PDE5 inhibitor in about 1 to about 20 mg unit dosage forms that, when orally administered, minimize undesired side effects previously believed unavoidable. These side effects include facial flushing, vision abnormalities, and a significant decrease in blood pressure when the PDE5 inhibitor is administered alone or in combination with an organic nitrate. The minimal effect of a present PDE5 inhibitor, administered in about 1 to about 20 mg unit dosage forms, on PDE6 also allows the administration of a selective PDE5 inhibitor to patients suffering from a retinal disease, like diabetic retinopathy or retinitis pigmentosa.

One such selective PDE5 inhibitor, i.e., (6R-trans)-6-(1,3-benzodioxol-5-yl)-2,3,6,7,12,12a-hexahydro-2-methylpyrazino[1',2':1,6]pyrido[3,4-b]indole-1,4-dione, alternatively named (6R,12aR)-2,3,6,7,12,12a-hexahydro-2-methyl-6-(3,4-methylene-dioxyphenyl)pyrazino[2',1':6,1]pyrido[3,4-b]indole-1,4-dione, is disclosed in Daugan U.S. Pat. No. 5,859,006, and represented by structural formula (I):

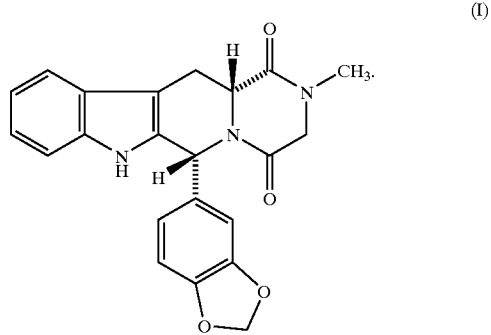

The compound of formula (I) was demonstrated in human clinical studies to exert a minimal impact on systolic blood pressure when administered in conjunction with organic nitrates. By contrast, sildenafil, when administered with nitrates, demonstrates as much as a four-fold greater decrease in systolic blood pressure over a placebo, which leads to the contraindications in the VIAGRA® insert, and in warnings to certain patients.

Selective PDE5 inhibitors vary significantly in chemical structure, and the use of a selective PDE5 inhibitor as defined in the present invention is not dependent on a particular chemical structure, but rather on the critical parameters outlined herein. However, preferred compounds having the required potency and selectivity can be readily identified by tests described herein from those described in Daugan U.S. Pat. No. 5,859,006, Daugan et al. U.S. Pat. No. 5,981,527, and Daugan et al. U.S. Pat. No. 6,001,847, each of which is incorporated herein by reference.

Preferred compounds of Daugan U.S. Pat. No. 5,859,006 and Daugan et al. U.S. Pat. No. 5,981,527 are represented by structural formula (II):

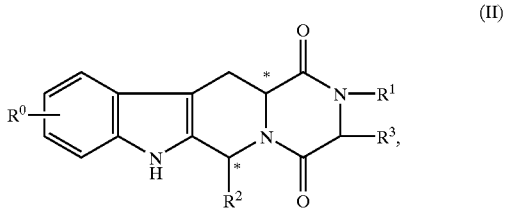

(II)

wherein $R^0$ is selected from the group consisting of hydrogen, halogen, and $C_{1-6}$alkyl;

$R^1$ is selected from the group consisting of hydrogen, $C_{1-6}$alkyl, $C_{2-6}$alkenyl, $C_{1-6}$alkynyl, halo-$C_{1-6}$alkyl, $C_{3-8}$cycloalkyl, $C_{3-8}$cycloalkyl$C_{1-3}$alkyl, aryl$C_{1-3}$alkyl, wherein aryl is phenyl or phenyl substituted with one to three substituents selected from the group consisting of halogen, $C_{1-6}$alkyl, $C_{1-6}$alkoxy, methylenedioxy, and mixtures thereof, and heteroaryl$C_{1-3}$alkyl, wherein heteroaryl is thienyl, furyl, or pyridyl, each optionally substituted with one to three substituents selected from the group consisting of halogen, $C_{1-6}$alkyl, $C_{1-6}$alkoxy, and mixtures thereof;

$R^2$ represents an optionally substituted monocyclic aromatic ring selected from benzene, thiophene, furan, and pyridine, or an optionally substituted bicyclic ring

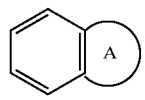

attached to the rest of the molecule via one of the benzene ring carbon atoms and wherein the fused ring A is a 5- or 6-membered ring, saturated or partially or fully unsaturated, and comprises carbon atoms and optionally one or two heteroatoms selected from the group consisting of oxygen, sulphur and nitrogen;

$R^3$ represents hydrogen or $C_{1-3}$alkyl, or $R^1$ and $R^3$ together represent a 3- or 4-membered alkyl or alkenyl chain; and salts and solvates thereof.

Other preferred compounds are those of formula (II) wherein:

$R^0$ is hydrogen, halogen, or $C_{1-6}$alkyl;

$R^1$ is hydrogen or $C_{1-6}$alkyl;

$R^2$ is the bicyclic ring

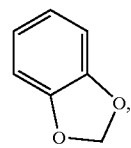

which can be optionally substituted by one or more groups selected from halogen and $C_{1-3}$alkyl; and $R^3$ is hydrogen or $C_{1-3}$alkyl.

The following Table 1 illustrates PDE5 and PDE6 $IC_{50}$ values for representative selective PDE5 inhibitors disclosed in U.S. Pat. No. 5,859,006, as determined by the procedures described herein.

TABLE 1

| Compound | PDE5 $IC_{50}$ (nM) | PDE6 $IC_{50}$ (nM) | PDE6/PDE5 |
|---|---|---|---|
| 1 | 5 | 663 | 133 |
| 2 | 2 | 937 | 469 |
| 3 | 2 | 420 | 210 |
| 4 | 5 | 729 | 146 |
| 5 | 2.5 | 3400 | 1360 |

Compound 5 in Table 1 has the structural formula (I) and additionally demonstrates an $IC_{50}$ against PDE1c of 10,000 and a ratio of PDE1c/PDE5 of 4,000.

The structures of Compound Nos. 1–5 in Table 1 are as in structural formula (II) wherein $R^0$, $R^1$, $R^2$, and $R^3$ are as follows:

-continued

| Compound | R⁰ | R¹ | R² | R³ |
|---|---|---|---|---|
| 3 | H | 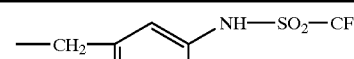 —CH₂—C₆H₄—NH—SO₂—CF₃ | 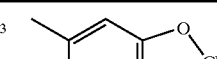 methylenedioxyphenyl | H |
| 4 | H | H | 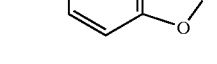 methylenedioxyphenyl | CH₃ |
| 5 | H | CH₃ | 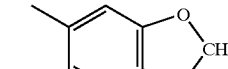 methylenedioxyphenyl | H |

The data in Table 1 indicate that a compound of structural formula (I), wherein $R^1$ is hydrogen or $C_{1-6}$alkyl, $R^2$ is

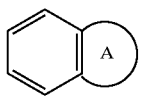

and $R^3$ is hydrogen is especially preferred. Preferably, A is

Preferred compounds are:
(6R,12aR)-2,3,6,7,12,12a-hexahydro-2-methyl-6-(3,4-methylenedioxyphenyl)pyrazino[2',1':6,1]pyrido[3,4-b]indole-1,4-dione; and
(3S,6R,12aR)-2,3,6,7,12,12a-hexahydro-2,3-dimethyl-6-(3,4-methylenedioxyphenyl)pyrazino[2',1':6,1]-pyrido[3,4-b]indole-1,4-dione; and physiologically acceptable salts and solvates (e.g., hydrates) thereof.

Other exemplary compounds useful in the present invention are those disclosed in Daugan et al. U.S. Pat. No. 6,001,847 and WO 97/43287, incorporated herein by reference.

Further exemplary compounds for use in the present invention are disclosed PCT application PCT/EP98/06050, which designates the U.S., entitled "Chemical Compounds," inventors A. Bombrun and F. Gellibert, the disclosure of which is specifically incorporated herein by reference. This class of compounds has the structural formula (III):

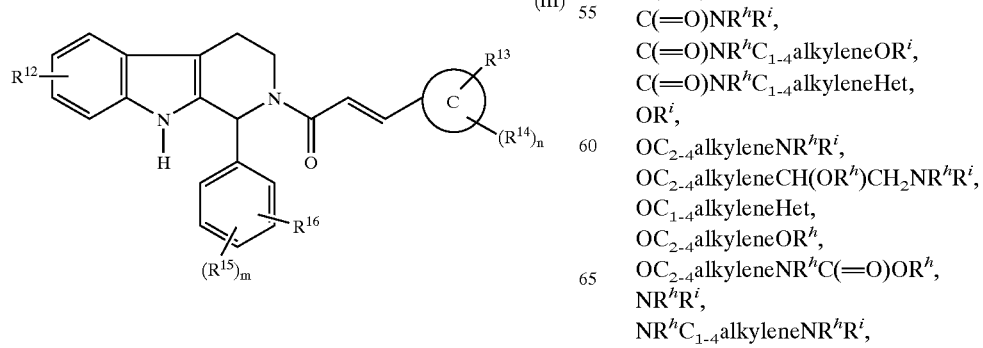

and salts and solvates (e.g., hydrates) wherein
C represents a 5- or 6-membered heteroaryl group containing at least one heteroatom selected from the group consisting of oxygen, nitrogen, and sulfur;
$R^{12}$ represents hydrogen or halogen;
$R^{13}$ is selected from the group consisting of
hydrogen,
nitro ($NO_2$),
trifluoromethyl,
trifluoromethoxy,
halogen,
cyano (CN),
a 5- or 6-membered heterocyclic group containing at least one heteroatom selected from the group consisting of oxygen, nitrogen, and sulphur, optionally substituted with $C(=O)OR^a$ or $C_{1-4}$alkyl,
$C_{1-6}$alkyl optionally substituted with $OR^h$,
$C_{1-3}$alkoxy,
$C(=O)R^h$,
$OC(=O)OR^h$,
$C(=O)OR^h$,
$C_{1-4}$alkyleneHet,
$C_{1-4}$alkyleneC(=O)OR^h$,
$OC_{1-4}$alkyleneC(=O)OR^h$,
$C_{1-4}$alkyleneOC_{1-4}$alkyleneC(=O)OR^h$,
$C(=O)NR^iSO_2R^j$,
$C(=O)C_{1-4}$alkyleneHet,
$C_{1-4}$alkyleneNR^hR^i$,
$C_{2-6}$alkenyleneNR^hR^i$,
$C(=O)NR^hR^i$,
$C(=O)NR^hR^i$,
$C(=O)NR^hC_{1-4}$alkyleneOR^i$,
$C(=O)NR^hC_{1-4}$alkyleneHet,
$OR^i$,
$OC_{2-4}$alkyleneNR^hR^i$,
$OC_{2-4}$alkyleneCH(OR^h)CH_2NR^hR^i$,
$OC_{1-4}$alkyleneHet,
$OC_{2-4}$alkyleneOR^h$,
$OC_{2-4}$alkyleneNR^hC(=O)OR^h$,
$NR^hR^i$,
$NR^hC_{1-4}$alkyleneNR^hR^i$, NR$^h$C(=O)R$^i$,
NR$^h$C(=O)NR$^h$R$^i$,
N(SO$_2$C$_{1-4}$alkyl)$_2$,
NR$^h$(SO$_2$C$_{1-4}$alkyl),
SO$_2$NR$^h$R$^i$,
and OSO$_2$trifluoromethyl;

R$^{14}$ is selected from the group consisting of hydrogen, halogen, OR$^h$, C$_{1-6}$alkyl, NO$_2$, and NR$^h$R$^i$;

or R$^{13}$ and R$^{14}$ are taken together to form a 3- or 4-membered alkylene or alkenylene chain component of a 5- or 6-membered ring, optionally containing at least one heteroatom;

R$^{15}$ is selected from the group consisting of hydrogen, halogen, NO$_2$, trifluoromethoxy, C$_{1-6}$alkyl, OC$_{1-6}$alkyl, and C(=O)OR$^h$;

R$^{16}$ is hydrogen, or R$^{15}$ and R$^{16}$ are taken together to form a 3- or 4-membered alkylene or alkenylene chain component of a 5- or 6-membered ring, optionally containing at least one heteroatom;

Het represents a 5- or 6-membered heterocyclic group containing at least one heteroatom selected from the group consisting of oxygen, nitrogen, and sulfur, and optionally substituted with C$_{1-4}$alkyl;

R$^h$ and R$^i$ can be the same or different and are independently selected from hydrogen and C$_{1-6}$alkyl;

R$^j$ represents phenyl or C$_{4-6}$cycloalkyl, wherein the phenyl or C$_{4-6}$cycloalkyl can be optionally substituted with one or more halogen atoms, one or more C(=O)OR$^h$, or one or more OR$^h$;

n is an integer 1, 2, or 3; and m is an integer 1 or 2.

Preparations

Human PDE5 Preparation

Recombinant production of human PDE5 was carried out essentially as described in Example 7 of U.S. Pat. No. 5,702,936, incorporated herein by reference, except that the yeast transformation vector employed, which is derived from the basic ADH2 plasmid described in V. Price et al., *Methods in Enzymology*, 1985, pages 308–318 (1990), incorporated yeast ADH2 promoter and terminator sequences rather than ADH1 promoter and terminator sequences and the *Saccharomyces cerevisiase* host was the protease-deficient strain BJ2-54 deposited on Aug. 31, 1998 with the American Type Culture Collection, Manassas, Va., under accession number ATCC 74465. Transformed host cells were grown in 2×SC-leu medium, pH 6.2, with trace metals, and vitamins. After 24 hours, YEP medium containing glycerol was added to a final concentration of 2×YEP/3% glycerol. Approximately 24 hours later, cells were harvested, washed, and stored at −70° C.

Cell pellets (29 g) were thawed on ice with an equal volume of lysis buffer (25 mM Tris-Cl, pH 8, 5 mM MgCl$_2$, 0.25 mM dithiothreitol, 1 mM benzamidine, and 10 μM ZnSO$_4$). Cells were lysed in a microfluidizer with N$_2$ at 20,000 psi. The lysate was centrifuged and filtered through 0.45 μm disposable filters. The filtrate was applied to a 150 mL column of Q Sepharose Fast Flow (Pharmacia). The column was washed with 1.5 volumes of Buffer A (20 mM Bis-Tris Propane, pH 6.8, 1 mM MgCl$_2$, 0.25 mM dithiothreitol, 10 μM ZnSO$_4$) and eluted with a step gradient of 125 mM NaCl in Buffer A followed by a linear gradient of 125–1000 mM NaCl in Buffer A.

Active fractions from the linear gradient were applied to a 180 mL hydroxyapatite column in Buffer B (20 mM Bis-Tris Propane (pH 6.8), 1 mM MgCl$_2$, 0.25 mM dithiothreitol, 10 μM ZnSO$_4$, and 250 mM KCl). After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8, 125 mM NaCl, 0.5 mM dithiothreitol, and 10 μM ZnSO$_4$). The pool was applied to a 140 mL column of Sephacryl S-300 HR and eluted with Buffer C. Active fractions were diluted to 50% glycerol and stored at −20° C. The resultant preparations were about 85% pure by SDS-PAGE.

Assay for PDE Activity

Activity of PDE5 can be measured by standard assays in the art. For example, specific activity of any PDE can be determined as follows. PDE assays utilizing a charcoal separation technique were performed essentially as described in Loughney et al., (1996), *The Journal of Biological Chemistry*, 271:796–806. In this assay, PDE5 activity converts [$^{32}$P]cGMP to [$^{32}$P]5'GMP in proportion to the amount of PDE5 activity present. The [$^{32}$P]5'GMP then is quantitatively converted to free [$^{32}$P] phosphate and unlabeled adenosine by the action of snake venom 5'-nucleotidase. Hence, the amount of [$^{32}$P] phosphate liberated is proportional to enzyme activity. The assay is performed at 30° C. in a 100 μL reaction mixture containing (final concentrations) 40 mM Tris-Cl (pH 8.0), 1 μM ZnSO$_4$, 5 mM MgCl$_2$, and 0.1 mg/mL bovine serum albumin. PDE5 is present in quantities that yield <30% total hydrolysis of substrate (linear assay conditions). The assay is initiated by addition of substrate (1 mM [$^{32}$P]cGMP), and the mixture is incubated for 12 minutes. Seventy-five (75) μg of *Crotalus atrox* venom then is added, and the incubation is continued for 3 more minutes (15 minutes total). The reaction is stopped by addition of 200 mL of activated charcoal (25 mg/mL suspension in 0.1 M NaH$_2$PO$_4$, pH 4). After centrifugation (750×g for 3 minutes) to sediment the charcoal, a sample of the supernatant is taken for radioactivity determination in a scintillation counter and the PDE5 activity is calculated. The preparations had specific activities of about 3 μmoles cGMP hydrolyzed per minute per milligram protein.

Bovine PDE6 Preparation

Bovine PDE6 was supplied by Dr. N. Virmaux, INSERM U338, Strasbourg. Bovine retinas were prepared as described by Virmaux et al., *FEBS Letters*, 12(6), pp. 325–328 (1971) and see also, A. Sitaramayya et al., *Exp. Eye Res.*, 25, pp. 163–169 (1977). Briefly, unless stated otherwise, all operations were done in the cold and in dim red light. Eyes were kept in the cold and in the dark for up to four hours after slaughtering.

Preparation of bovine retinal outer segment (ROS) basically followed procedures described by Schichi et al., *J. Biol. Chem.*, 224:529 (1969). In a typical experiment, 35 bovine retinas were ground in a mortar with 35 mL 0.066 M phosphate buffer, pH 7.0, made up to 40% with sucrose, followed by homogenization in a Potter homogenizer (20 up and down strokes). The suspension was centrifuged at 25,000×g for 20 minutes. The pellet was homogenized in 7.5 mL 0.006 M phosphate buffer (40% in sucrose), and carefully layered under 7.5 mL of phosphate buffer (containing no sucrose). Centrifugation was conducted in a swing-out rotor at 45,000×g for 20 minutes, and produced a pellet which is black at the bottom, and also a red band at the interface 0.066 M. phosphate—40% sucrose/0.066 M phosphate (crude ROS). The red material at the interface was removed, diluted with phosphate buffer, spun down to a pellet, and redistributed in buffered 40% sucrose as described above. This procedure was repeated 2 or 3 times until no pellet was formed. The purified ROS was washed in phosphate buffer and finally spun down to a pellet at 25,000×g for 20 minutes. All materials were then kept frozen until used.

Hypotonic extracts were prepared by suspending isolated ROS in 10 mM Tris-Cl pH 7.5, 1 mM EDTA, and 1 mM dithioerythritol, followed by centrifugation at 100,000×g for 30 minutes.

The preparation was reported to have a specific activity of about 35 nmoles cGMP hydrolyzed per minute per milligram protein.

PDE1c Preparation from Spodoptera fugiperda Cells (Sf9)

Cell pellets (5g) were thawed on ice with 20 ml of Lysis Buffer (50 mM MOPS pH 7.4, 10 μM $ZnSO_4$, 0.1 mM $CaCl_2$, 1 mM DTT, 2 mM benzamidine HCl, 5μg/ml each of pepstatin, leupeptin, and aprotenin). Cells were lysed by passage through a French pressure cell (SLM-Aminco) while temperatures were maintained below 10° C. The resultant cell homogenate was centrifuged at 36,000 rpm at 4° C. for 45 minutes in a Beckman ultracentrifuge using a Type TI45 rotor. The supernatant was discarded and the resultant pellet was resuspended with 40 ml of Solubilization Buffer (Lysis Buffer containing 1M NaCl, 0.1M $MgCl_2$, 1 mM $CaCl_2$, 20 μg/ml calmodulin, and 1% Sulfobetaine SB12 (Z3-12) by sonicating using a VibraCell tuner with a microtip for 3×30 seconds. This was performed in a crushed ice/salt mix for cooling. Following sonication, the mixture was slowly mixed for 30 minutes at 4° C. to finish solubilizing membrane bound proteins. This mixture was centrifuged in a Beckman ultracentrifuge using a type TI45 rotor at 36,000 rpm for 45 minutes. The supernatant was diluted with Lysis Buffer containing 10 μg/ml calpain inhibitor I and II. The precipitated protein was centrifuged for 20 minutes at 9,000 rpm in a Beckman JA-10 rotor. The recovered supernatant then was subjected to Mimetic Blue AP Agarose Chromatography.

In order to run the Mimetic Blue AP Agarose Column, the resin initially was shielded by the application of 10 bed volumes of 1% polyvinyl-pyrrolidine (i.e., MW of 40,000) to block nonspecific binding sites. The loosely bound PVP-40 was removed by washing with 10 bed volumes of 2M NaCl, and 10 mM sodium citrate pH 3.4. Just prior to addition of the solubilized PDE1c sample, the column was equilibrated with 5 bed volumes of Column Buffer A (50 mM MOPS pH 7.4, 10 μM $ZnSO_4$, 5 mM $MgCl_2$, 0.1 mM $CaCl_2$, 1 mM DTT, 2 mM benzamidine HCl).

The solubilized sample was applied to the column at a flow rate of 2 ml/min with recycling such that the total sample was applied 4 to 5 times in 12 hours. After loading was completed, the column was washed with 10 column volumes of Column Buffer A, followed by 5 column volumes of Column Buffer B (Column Buffer A containing 20 mM 5'-AMP), and followed by 5 column volumes of Column Buffer C (50 mM MOPS pH 7.4, 10 μM $ZnSO_4$, 0.1 mM $CaCl_2$, 1 mM dithiothreitol, and 2 mM benzamidine HCl). The enzyme was eluted into three successive pools. The first pool consisted of enzyme from a 5 bed volume wash with Column Buffer C containing 1 mM cAMP. The second pool consisted of enzyme from a 10 bed volume wash with Column Buffer C containing 1 M NaCl. The final pool of enzyme consisted of a 5 bed volume wash with Column Buffer C containing 1 M NaCl and 20 mM cAMP.

The active pools of enzyme were collected and the cyclic nucleotide removed via conventional gel filtration chromatography or chromatography on hydroxy-apatite resins. Following removal of cyclic nucleotides, the enzyme pools were dialyzed against Dialysis Buffer containing 25 mM MOPS pH 7.4, 10 μM $ZnSO_4$, 500 mM NaCl, 1 mM $CaCl_2$, 1 mM dithiothreitol, 1 mM benzamidine HCl, followed by dialysis against Dialysis buffer containing 50% glycerol. The enzyme was quick frozen with the aid of dry ice and stored at −70° C.

The resultant preparations were about >90% pure by SDS-PAGE. These preparations had specific activities of about 0.1 to 1.0 μmol cAMP hydrolyzed per minute per milligram protein.

$IC_{50}$ Value Determinations

The parameter of interest in evaluating the potency of a competitive enzyme inhibitor of PDE5 and/or PDE1c and PDE6 is the inhibition constant, i.e., $K_i$. This parameter can be approximated by determining the $IC_{50}$, which is the inhibitor concentration that results in 50% enzyme inhibition, in a single dose-response experiment under the following conditions.

The concentration of inhibitor is always much greater than the concentration of enzyme, so that free inhibitor concentration (which is unknown) is approximated by total inhibitor concentration (which is known).

A suitable range of inhibitor concentrations is chosen (i.e., inhibitor concentrations at least several fold greater and several fold less than the $K_i$ are present in the experiment). Typically, inhibitor concentrations ranged from 10 nM to 10 μM.

The concentrations of enzyme and substrate are chosen such that less than 20% of the substrate is consumed in the absence of inhibitor (providing, e.g., maximum substrate hydrolysis of from 10 to 15%), so that enzyme activity is approximately constant throughout the assay.

The concentration of substrate is less than one-tenth the Michaelis constant ($K_m$). Under these conditions, the $IC_{50}$ will closely approximate the $K_i$. This is because of the Cheng-Prusoff equation relating these two parameters: $IC_{50}=K_i (1+S/K_m)$, with $(1+S/K_m)$ approximately 1 at low values of $S/K_m$.

The $IC_{50}$ value is estimated from the data points by fitting the data to a suitable model of the enzyme inhibitor interaction. When this interaction is known to involve simple competition of the inhibitor with the substrate, a two-parameter model can be used:

$$Y=A/(1+x/B)$$

where the y is the enzyme activity measured at an inhibitor concentration of x, A is the activity in the absence of inhibitor and B is the $IC_{50}$. See Y. Cheng et al., *Biochem. Pharmacol.*, 22:3099–3108 (1973).

Effects of inhibitors of the present invention on enzymatic activity of PDE5 and PDE6 preparations as described above were assessed in either of two assays which differed from each other principally on the basis of scale and provided essentially the same results in terms of $IC_{50}$ values. Both assays involved modification of the procedure of Wells et al., *Biochim. Biophys. Acta,* 384:430 (1975). The first of the assays was performed in a total volume of 200 μl containing 50 mM Tris pH 7.5, 3 mM Mg acetate, 1 mM EDTA, 50 μg/mL snake venom nucleotidase and 50 nM [$^3$H]-cGMP (Amersham). Compounds of the invention were dissolved in DMSO finally present at 2% in the assay. The assays were incubated for 30 minutes at 30° C. and stopped by addition of 800 μl of 10 mM Tris pH 7.5, 10 mM EDTA, 10 mM theophylline, 0.1 mM adenosine, and 0.1 mM guanosine. The mixtures were loaded on to 0.5 mL QAE Sephadex columns, and eluted with 2 mL of 0.1 M formate (pH 7.4).

The eluted radioactivity was measured by scintillation counting in Optiphase Hisafe 3.

A second, microplate, PDE assay was developed using Multiscreen plates and a vacuum manifold. The assay (100 µl) contained 50 mM Tris pH 7.5, 5 mM Mg acetate, 1 mM EDTA and 250 µg/mL snake venom nucleotidase. The other components of the reaction mixture were as described above. At the end of the incubation, the total volume of the assays were loaded on a QAE Sephadex microcolumn plate by filtration. Free radioactivity was eluted with 200 µl of water from which 50 µl aliquots were analyzed by scintillation counting as described above.

The following examples are presented to further illustrate the preparation of the claimed invention. The scope of the present invention is not to be construed as merely consisting of the following examples.

EXAMPLE 1

The compound of structural formula (I) was prepared as described in U.S. Pat. No. 5,859,006 and formulated in tablets using wet granulation. Povidone was dissolved in water to make a 10% solution. The active compound, microcrystalline cellulose, croscarmellose sodium, and sodium lauryl sulfate were added to a high shear mixer and mixed for 2 minutes. The powders were wet granulated with the povidone solution and extra water as required to complete the granulation. The resultant mixture was dried in a fluid bed drier with inlet air at 70° C.±5° C. until the loss on drying was below 2.5%. The granules were passed through a Comil with a suitable screen (or a sieve) and added to a suitable mixer. The extragranular croscarmellose sodium and sodium lauryl sulfate, and the colloidal anhydrous silica were passed through a suitable sieve (e.g., 500 micron) and added to the mixer and blended 5 minutes. Magnesium stearate was added and blended for 2 minutes. The blend was compressed to a target compression/weight of 250 mg using 9 mm round normal concave tooling.

The core tablets were coated with an aqueous suspension of Opadry OY-S-7322 using an Accelacota (or similar coating pan) using inlet air at 50° C. to 70° C. until the tablet weight was increased by approximately 8 mg. Opadry OY-S-7322 contains methylhydroxypropylcellulose Ph.Eur., titanium dioxide Ph. Eur., Triacetin USP. Opadry increases the weight of each tablet to about 258 mg. The amount of film coat applied per tablet may be less than that stated depending on the process efficiency.

The tablets are filled into blister packs and accompanied by package insert describing the safety and efficacy of the compound.

| Component | Formulations (mg per tablet) | |
| --- | --- | --- |
| Selective PDE5 Inhibitor[1] | 1 | 5 |
| Hydroxypropylmethylcellulose phthalate | 1 | 5 |
| Microcrystalline Cellulose | 221.87 | 213.87 |
| Croscarmellose Sodium | 5.00 | 5.00 |
| Sodium Lauryl Sulfate | 2.50 | 2.50 |
| Sulfate Povidone K30 | 9.38 | 9.38 |
| Purified Water, USP (water for irrigation) | q.s. | q.s. |
| Croscarmellose Sodium | 5.00 | 5.00 |
| Sodium Lauryl Sulfate | 2.50 | 2.50 |
| Colloidal Anhydrous Silica | 0.50 | 0.50 |
| Magnesium Stearate | 1.25 | 1.25 |
| Total core subtotal | 250.00 | 250.00 |
| (Film coat Opadry OY-S-7322) | about 8 mg | about 8 mg |

[1]Compound of structural formula (I).

EXAMPLE 2

The following formula is used in preparing a finished dosage form containing 10 mg of the compound of structural formula (I).

| Ingredient | Quantity (mg) |
| --- | --- |
| Granulation | |
| Selective PDE5 Inhibitor[1] | 10.00 |
| Lactose Monohydrate | 153.80 |
| Lactose Monohydrate (spray dried) | 25.00 |
| Hydroxypropylcellulose | 4.00 |
| Croscarmellose Sodium | 9.00 |
| Hydroxypropylcellulose (EF) | 1.75 |
| Sodium Lauryl Sulfate | 0.70 |
| | 35.00 |
| Outside Powders | |
| Microcrystalline Cellulose (granular-102) | 37.50 |
| Croscarmellose Sodium | 7.00 |
| Magnesium Stearate (vegetable) | 1.25 |
| Total | 250 mg |

Film coat (approximately) 11.25

Purified Water, USP is used in the manufacture of the tablets. The water is removed during processing and minimal levels remain in the finished product.

Tablets are manufactured using a wet granulation process. A step-by-step description of the process is as follows. The drug and excipients to be granulated are security sieved. The selective PDE5 inhibitor is dry blended with lactose monohydrate (spray dried), hydroxypropylcellulose, croscarmellose sodium, and lactose monohydrate. The resulting powder blend is granulated with an aqueous solution of hydroxypropylcellulose and sodium lauryl sulfate using a Powrex or other suitable high shear granulator. Additional water can be added to reach the desired endpoint. A mill can be used to delump the wet granulation and facilitate drying. The wet granulation is dried using either a fluid bed dryer or a drying oven. Once the material is dried, it can be sized to eliminate any large agglomerates. Microcrystalline cellulose, croscarmellose sodium, and magnesium stearate are security sieved and added to the dry sized granules. These excipients and the dry granulation are mixed until uniform using a tumble bin, ribbon mixer, or other suitable mixing equipment. The mixing process can be separated into two phases. The microcrystalline cellulose, croscarmellose sodium, and the dried granulation are added to the mixer and blended during the first phase, followed by the addition of the magnesium stearate to this granulation and a second mixing phase.

The mixed granulation then is compressed into tablets using a rotary compression machine. The core tablets are film coated with an aqueous suspension of the appropriate color mixture in a coating pan (e.g., Accela Cota). The coated tablets can be lightly dusted with talc to improve tablet handling characteristics.

The tablets are filled into plastic containers (30 tablets/container) and accompanied by package insert describing the safety and efficacy of the compound.

EXAMPLE 3

The following formula is used in preparing a finished dosage form of 5 mg of the compound of structural formula (I).

| Ingredient | Quantity (mg) |
|---|---|
| Granulation | |
| Selective PDE5 Inhibitor[1] | 2.50 |
| Lactose Monohydrate | 79.395 |
| Lactose Monohydrate (spray dried) | 12.50 |
| Hydroxypropylcellulose | 2.00 |
| Croscarmellose Sodium | 4.50 |
| Hydroxypropylcellulose (EF) | 0.875 |
| Sodium Lauryl Sulfate | 0.35 |
| Outside Powders | |
| Microcrystalline Cellulose (granular-102) | 18.75 |
| Croscarmellose Sodium | 3.50 |
| Magnesium Stearate (vegetable) | 0.63 |
| Total | 125 mg |

Film coat (approximately) 6.875

The dosage form of Example 3 was prepared in an identical manner to the dosage form of Example 2.

EXAMPLE 4

| | Solution Capsule | |
|---|---|---|
| Ingredient | mg/Capsule | Percent (%) |
| Selective PDE5 Inhibitor[1] | 10 | 2 |
| PEG400 NF | 490 | 98 |
| Fill Weight | 500 | 100 |

The gelatin capsules are precisely filled by pumping an accurate fill volume of pre-dissolved drug formulation into the partially sealed cavity of a capsule. Immediately following injection fill of the drug solution formulation, the capsule is completely heat sealed.

The capsules are filled into plastic containers and accompanied by a package insert.

EXAMPLE 5

This study was a randomized, double-blind, placebo-controlled, two-way crossover design clinical pharmacology drug interaction study that evaluated the hemodynamic effects of concomitant administration of a selective PDE5 inhibitor Study Drug (i.e., the compound of structural formula (I)) and short-acting nitrates on healthy male volunteers. In this study, the subjects received either the Study Drug at a dose of 10 mg or a placebo, daily for seven days. On the sixth or seventh day, the subjects received sublingual nitroglycerin (0.4 mg) while supine on a tilt table. The nitroglycerin was administered 3 hours after Study Drug dosing, and all subjects kept the nitroglycerin tablet under their tongue until it completely dissolved. The subjects were tilted to 70° head-up every 5 minutes for a total of 30 minutes with measurement of blood pressure and heart rate. There were no discontinuations among the twenty-two healthy male subjects (ages 19 to 60 years old) that entered this study.

In a preliminary analysis of this study, the Study Drug was well tolerated and there were no serious adverse events. There were no Study Drug-associated changes in laboratory safety assessments or 12-lead ECGs. The most common adverse events were headache, dyspepsia, and back pain. The study demonstrated minimal effects on mean systolic blood pressure and on mean maximal nitroglycerin-induced decrease in systolic blood pressure and the maximal nitroglycerin-induced decrease in systolic blood pressure among all patients.

EXAMPLE 6

In two randomized, double-blinded placebo controlled studies, the compound of structural formula (I), at a range of doses in both daily dosing and for on demand therapy for sexual encounters and intercourse in the home setting, was administered to patients in need thereof. Doses from 5 to 20 mg of the compound of structural formula (I) were efficacious and demonstrated no flushing and no reports of vision abnormalities. It was found that a 10 mg dose of the compound of structural formula (I) was fully efficacious and demonstrated minimal side effects (no flushing and no reports of blue vision).

Erectile function was assessed by the International Index of Erectile Function (IIEF) (Rosen et al., Urology, 49, pp. 822–830 (1997)), diaries of sexual attempts, and a global satisfaction question. The compound of structural formula (I) significantly improved erectile function as assessed by all endpoints. In both "on demand" and daily dose regimens, the compound of structural formula (I) significantly improved erectile function in doses between 1 and 20 mg.

EXAMPLE 7

A third clinical study was a randomized, double-blind, placebo-controlled study using a compound of structural formula (I) (Study Drug) administered "on demand" to patients with male erectile dysfunction. The Study Drug was administered over a period of eight weeks in the treatment of male erectile dysfunction (ED). Erectile dysfunction (ED) is defined as the persistent inability to attain and/or maintain an erection adequate to permit satisfactory sexual performance. "On demand" dosing is defined as intermittent administration of Study Drug prior to expected sexual activity.

The study population consisted of 212 men, at least 18 years of age, with mild to severe erectile dysfunction. The Study Drug was orally administered as tablets of coprecipitate made in accordance with Butler U.S. Pat. No. 5,985,326. The Study Drug was administered in 2 mg, 5 mg, 10 mg, and 25 mg doses, "on demand" and not more than once every 24 hours. Treatment with all nitrates, azole antifungals (e.g., ketoconazole or itraconazole), warfarin, erythromycin, or antiandrogens was not allowed at any time during the study. No other approved or experimental medications, treatments, or devices used to treat ED were allowed. Forty-one subjects were administered a placebo.

The two primary efficacy variables were the ability of a subject to penetrate his partner and his ability to maintain an erection during intercourse, as measured by the International Index of Erectile Function (IIEF). The IIEF Questionnaire contains fifteen questions, and is a brief, reliable measure of erectile function. See R. C. Rosen et al., *Urology*, 49, pp. 822–830 (1997).

Secondary efficacy variables were IIEF domain scores for erectile function, orgasmic function, sexual desire, intercourse satisfaction, and overall satisfaction; the patient's ability to achieve an erection, ability to insert his penis into his partner's vagina, completion of intercourse with ejaculation, satisfaction with the hardness of his erection, and overall satisfaction, all as measured by the Sexual Encounter Profile (SEP) diary; and a global assessment question asked at the end of the treatment period. The SEP is a patient diary instrument documenting each sexual encounter during the course of the study.

The safety analysis of the study included all enrolled subjects, and was assessed by evaluating all reported adverse events, and changes in clinical laboratory values, vital signs, physical examination results, and electrocardiogram results.

At endpoint, patients who rated their penetration ability (IIEF Question 3) as "almost always or always" were as follows: 17.5% in the placebo group, 38.1% in the 2 mg group, 48.8% in the 5 mg group, 51.2% in the 10 mg group, and 83.7% in the 25 mg group. Comparisons revealed statistically significant differences in change in penetration ability between placebo and all dose levels of the Study Drug.

At endpoint, patients who rated their ability to maintain an erection (IIEF Question 4) during intercourse as "almost always or always" are as follows: 10.0% in the placebo group, 19.5% in the 2 mg group, 32.6% in the 5 mg group, 39.0% in the 10 mg group, and 69.0% in the 25 mg group. Comparison revealed statistically significant differences in change in penetration ability between placebo and the three higher dose levels of Study Drug.

Overall, this study demonstrated that all four doses of Study Drug, namely 2 mg, 5 mg, 10 mg, and 25 mg, taken "on demand" produced significant improvement, relative to placebo, in the sexual performance of men with erectile dysfunction as assessed by the IIEF, by patient diaries assessing frequency of successful intercourse and intercourse satisfaction, and by a global assessment. This improvement was demonstrated in a broad study population that included patients who exhibited all severities of erectile dysfunction. Most adverse events were mild or moderate in severity. Significantly, no adverse events related to color vision disturbances were reported by any patient.

The combined results from clinical studies showed that administration of a compound of structural formula (I) effectively treats male erectile dysfunction, as illustrated in the following table.

| IIEF ERECTILE FUNCTION DOMAIN (Change from Baseline) | | | |
|---|---|---|---|
| Unit Dose | n | Mean ± SD | p |
| placebo | 131 | 0.8 ± 5.3 | |
| 2 mg | 75 | 3.9 ± 6.1 | <.001 |
| 5 mg | 79 | 6.6 ± 7.1 | <.001 |
| 10 mg | 135 | 7.9 ± 6.7 | <.001 |
| 25 mg | 132 | 9.4 ± 7.0 | <.001 |
| 50 mg | 52 | 9.8 ± 5.5 | <.001 |
| 100 mg | 49 | 8.4 ± 6.1 | <.001 | n is number of subjects, SD is standard deviation.

However, it also was observed from the combined clinical studies that the percent of treatment-emergent adverse events increased with an increasing unit dose of the compound of structural formula (I), as illustrated in the following table.

| Treatment-Emergent Adverse Events (%) | | | | | | | |
|---|---|---|---|---|---|---|---|
| | | Unit Dose (mg) | | | | | |
| Event | Placebo | 2 | 5 | 10 | 25 | 50 | 100 |
| Headache | 10 | 12 | 10 | 23 | 29 | 34 | 46 |
| Dyspepsia | 6 | 3 | 14 | 13 | 19 | 20 | 25 |
| Back Pain | 5 | 3 | 3 | 15 | 18 | 24 | 22 |
| Myalgia | 3 | 0 | 3 | 9 | 16 | 20 | 29 |
| Rhinitis | 3 | 7 | 3 | 4 | 4 | 0 | 2 |
| Conjunctivitis | 1 | 0 | 1 | 1 | 0 | 2 | 5 |
| Eyelid Edema | 0 | 0 | 0 | 1 | 1 | 2 | 3 |
| Flushing | 0 | 0 | 0 | <1 | 0 | 3 | 7 |
| Vision Abnormalities | 0 | 0 | 0 | 0 | 0 | 0 | 0 |

The above table shows an increase in adverse events at 25 mg through 100 mg unit doses. Accordingly, even though efficacy in the treatment of ED was observed at 25 mg to 100 mg doses, the adverse events observed from 25 mg to 100 mg doses must be considered.

In accordance with the present invention, a unit dose of about 1 to about 20 mg, preferably about 2 to about 20 mg, more preferably about 5 to about 20 mg, and most preferably about 5 to about 15 mg, administered up to a maximum of 20 mg per 24-hour period, both effectively treats ED and minimizes or eliminates the occurrence of adverse side effects. Importantly, no vision abnormalities were reported and flushing was essentially eliminated. Surprisingly, in addition to treating ED in individuals, with about 1 to about 20 mg unit dose of the compound of structural formula (I), with a minimum of adverse side effects, individuals undergoing nitrate therapy also can be treated for ED by the method and composition of the present invention.

The principles, preferred embodiments, and modes of operation of the present invention have been described in the foregoing specification. The invention intended to be protected herein, however, is not construed to be limited to the particular forms disclosed, because they are to be regarded as illustrative rather than restrictive. Variations and changes may be made by those skilled in the art without departing from the spirit of the invention.

What is claimed is:

1. A method of treating sexual dysfunction in an individual suffering from a retinal disease comprising administering an oral dosage form comprising about 1 to about 20 mg of a selective PDE5 inhibitor having
    (i) at least a 100-fold differential in $IC_{50}$ values for the inhibition of PDE5 versus PDE6,
    (ii) at least 1000-fold differential in $IC_{50}$ values for the inhibition of PDE5 versus PDE1c,
    (iii) an $IC_{50}$ less than 10 nM, and
    (iv) a sufficient bioavailability to be effective in about 1 to about 20 mg unit oral dosages.

2. The method of claim 1 wherein the retinal disease is diabetic retinopathy.

3. The method of claim 1 wherein the retinal disease is retinitis pigmentosa.

4. A method of treating sexual dysfunction in an individual suffering from a condition selected from the group consisting of class 1 congestive heart failure, a myocardial infarction within 90 days before onset of the sexual dysfunction treatment, and combinations thereof comprising administering an oral dosage from comprising about 1 to about 20 mg of a selective PDE5 inhibitor having (i) at least a 100-fold differential in $IC_{50}$ values for the inhibition of PDE5 versus PDE6, (ii) at least 1000-fold differential in $IC_{50}$ values for the inhibition of PDE5 versus PDE1c, (iii) an IC50 less than 10 nM, and (iv) a sufficient bioavailability to be effective in about 1 to about 20 mg unit oral dosages.

5. The method of claims 1 or 4 wherein the oral dosage form comprises about 5 mg, about 10 mg, or about 20 mg, of a selective PDE5 inhibitor.

6. The method of claim 1 or 4 wherein the maximum dosage of the selective PDE5 inhibitor is about 20 mg per 24-hour period.

7. The method of claim 1 or 4 wherein the selective PDE5 inhibitor has the structure

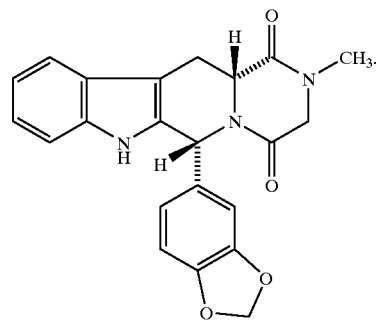

(I)

\* \* \* \* \*

UNITED STATES PATENT AND TRADEMARK OFFICE
CERTIFICATE OF CORRECTION

PATENT NO.    : 6,451,807 B1
DATED         : September 17, 2002
INVENTOR(S)   : Jeffrey T. Emmick et al.

It is certified that error appears in the above-identified patent and that said Letters Patent is hereby corrected as shown below:

Title page,
Item [75], Inventors, "Woodinvill," should be -- Woodinville, --,
Item [56], References Cited, OTHER PUBLICATIONS, "Cheng et al." reference, "[six]" should be -- [sic] --; "Webb et al." reference, "regults" should be -- results --; and insert the following references:
-- Goldenberg, "Safety and efficacy of sildenafil citrate in the treatment of male erectile dysfunction," *Clinical Therapeutics, 20*, No. 6, pp. 1033-1048 (1998).

Israel, "Viagra: The first oral treatment for impotence," *The Pharmaceutical Journal, 261*, pp. 164-165 (1998).

Product Insert, "VIAGRA® Tablets (2000). --

Signed and Sealed this

Twenty-seventh Day of April, 2004

JON W. DUDAS
*Acting Director of the United States Patent and Trademark Office*